US010695022B2

(12) United States Patent
Budoff et al.

(10) Patent No.: US 10,695,022 B2
(45) Date of Patent: Jun. 30, 2020

(54) METHOD FOR THORACIC VERTEBRAL BONE DENSITY MEASUREMENT BY THORACIC QUANTITATIVE COMPUTED TOMOGRAPHY

(71) Applicant: Los Angeles BioMedical Research Institute at Harbor-UCLA Medical Center, Torrance, CA (US)

(72) Inventors: Matthew J. Budoff, Manhattan Beach, CA (US); Song Shou Mao, Lakewood, CA (US); Christopher A. Dailing, Long Beach, CA (US)

(73) Assignee: Los Angeles BioMedical Research Institute at Harbor-UCLA Medical Center, Torrance, CA (US)

( * ) Notice: Subject to any disclaimer, the term of this patent is extended or adjusted under 35 U.S.C. 154(b) by 20 days.

(21) Appl. No.: 15/442,596

(22) Filed: Feb. 24, 2017

(65) Prior Publication Data

US 2017/0164918 A1 Jun. 15, 2017

Related U.S. Application Data

(63) Continuation of application No. 14/806,472, filed on Jul. 22, 2015, now abandoned, which is a
(Continued)

(51) Int. Cl.
*A61B 6/00* (2006.01)
*A61B 5/00* (2006.01)
(Continued)

(52) U.S. Cl.
CPC ............ *A61B 6/505* (2013.01); *A61B 5/4509* (2013.01); *A61B 5/4566* (2013.01); *A61B 6/032* (2013.01);
(Continued)

(58) Field of Classification Search
None
See application file for complete search history.

(56) References Cited

U.S. PATENT DOCUMENTS 8,244,361 B1 8/2012 De Ridder
2005/0015002 A1 1/2005 Dixon et al.

OTHER PUBLICATIONS

Boden et al., "Precise Measurement of Vertebral Bone Density Using Computed Tomography Without the Use of an External Reference Phantom", Journal of Digital Imaging, vol. 2, No. 1, 1989, pp. 31-38.*

(Continued)

*Primary Examiner* — Katherine L Fernandez
(74) *Attorney, Agent, or Firm* — Pillsbury Winthrop Shaw Pittman LLP

(57) ABSTRACT

A technique for measuring thoracic vertebral bone density (BMD) and coronary calcium score (CCS). Representatively, BMD was measured and averaged at three consecutive thoracic spines (3T) starting from the left main coronary artery caudally and averaging the results of the measurements at the first, second and third spine regions to obtain a thoracic trabecular bone mineral density measurement. The "reference", as the 3T BMD value of 30 year old and the piBMD (predicted individual BMD (piBMD) were developed. Based on the "reference", and piBMD, T and Z score of 3T formula were derived in both genders. The new calibration phantom of TQCT and LQCT was designed. The ratios of CTHU/mg/cc were obtained with varying scanners, which were used to translate the CTHU to density units (mg/cc) in BMD and CCS mass measurement. A processor capable of quantitating both BMD and CCS burden was designed. In image without a calibration phantom, formulas were created to quantitate BMD with a high precision.

21 Claims, 6 Drawing Sheets

Related U.S. Application Data continuation of application No. 13/031,047, filed on Feb. 18, 2011, now Pat. No. 9,119,590.

(60) Provisional application No. 61/305,698, filed on Feb. 18, 2010.

(51) Int. Cl.
  A61B 6/03   (2006.01)
  A61B 6/04   (2006.01)
  G01N 23/046 (2018.01)
  G06K 9/52   (2006.01)
  G06K 9/62   (2006.01)
  G06K 9/46   (2006.01)

(52) U.S. Cl.
  CPC .......... *A61B 6/0407* (2013.01); *A61B 6/4435* (2013.01); *A61B 6/504* (2013.01); *A61B 6/5205* (2013.01); *A61B 6/5217* (2013.01); *G01N 23/046* (2013.01); *G06K 9/52* (2013.01); *G06K 9/6267* (2013.01); *A61B 6/5294* (2013.01); *G06K 2009/4666* (2013.01); *G06K 2209/05* (2013.01)

(56) References Cited

OTHER PUBLICATIONS

Hui et al., "Universal Standardization of Bone Density Measurements: A Method with Optimal Properties for Calibration Among Several Instruments", Journal of Bone and Mineral Research, vol. 12, No. 9, 1997, pp. 1463-1470.*

Bauer et al., "Volumetric Quantitative CT of the Spine and Hip Derived from Contrast-Enhanced MDCT: Conversion Factors", Musculoskeletal Imaging, vol. 188, May 2007, pp. 1294-1301.*

Budoff, MJ, et al., "Assessment of coronary artery disease by cardiac computed tomography: a scientific statement from the American Heart Association Committee on Cardiovascular Imaging and Intervention", Council on Cardiovascular Radiology and Intervention, and Committee on Cardiac Imaging, Council on Clinical Cardiology. Circulation, 114(16), (Oct. 17, 2006), 1761-91.

Cann, CE, et al., "Precise measurement of vertebral mineral content using computed tomography", J. Comput Assist Tomogr., 4(4), (Aug. 1980), 493-500.

Engelke, K, et al., "Significance of QCT bone mineral density and its standard deviation as parameters to evaluate osteoporosis", J Comput Assist Tomogr., 19(1), (Jan.-Feb. 1995), 111-116.

Genant, H. K., et al., "Noninvasive assessment of bone mineral and structure: state. of the art", J Bone Miner Res, 11 (6), (Jun. 1996), 707-730.

Grampp, S., et al., "Quantitative CT assessment of the lumbar spine and radius in patients with osteoporosis", Am J Roentgenol, 167(1), (Jul. 1996)•, 133-140.

Grampp, S., et al., "Radiologic diagnosis of osteoporosis. Current methods and perspectives.", Radial Clin North Am., 31(5), (Sep. 1993), 1133-1145.

Guerci, A. D., et al., "Comparison of electron beam computed tomography scanning and conventional risk factor assessment for the prediction of angiographic coronary artery disease", J Am Coli Cardiol, 32, (1998), 673-679.

Ismail, A. A., et al., "Number and type of vertebral deformities: epidemiological characteristics and relation to back pain and height loss", European Vertebral Osteoporosis Study Group; Osteoporo Int., 9(3),—(1999), 206-213.

Lang, T. F., et al., "Assessment of vertebral bone mineral density using volumetric quantitative CT", J Com put Assist Tomogr., 23(1), (Jan.-Feb. 1999), 130-137.

Laval-Jeantet, M., et al., An experimental study to evalu.ate mineralization of vertebral bone by computerized tomographyl J Radial, 60(2), (Feb. 1979), 87-93.

Lenchik, L., et al., "Measurement of trabecular bone mineral density in the thoracic spine using cardiac gated quantitative computed tomography", J. Comput Assist Tomogr., 28(1), (Jan.-Feb. 2004), 134-139.

Mann, T., et al., "Vertebral deformity in men", J Bone Miner Res., 7(11 ), (Nov. 1992), 1259-1265.

Marcus, R., et al., "The Nature of Osteoporosis", Third Edition; Elsevier, Ch. 2, (2008), 27-36.

Melton III, L. J., et al., "Epidemiology of vertebral fractures in women", Am J Epidemiol., 129(5}, (May 1989), 1000-1011.

Mel Ton III, L. J., et al., "Relative contributions of bone density, bone turnover, and clinical risk factors to long-term fracture prediction", J Bone Miner Res, 18(2), (Feb. 2003), 312-318.

O'Malley, P. G., et al., "Prognostic value of coronary electron-beam computed tomography for coronary heart disease events in asymptomatic populations", Am J Cardiol, 85, (2000), 945-948.

Parfitt, a. M., "Bone remodeling: Relationship to the amount and structure of bone, and the pathogenesis and prevention of fractures", Osteoposis, Etiology, Diagnosis, and Management (B.L. Ragg and L.J. Melton III Eds.), Raven Press, New York, (1988), 45-93.

Penrod, J. et al., "Demographic Perspectives: the magnitude of concern", Osteoporosis: Clinical Prevention, Diagnosis and Management, Springer Publishing Co., (2008), 9-18.

Wong, M. , et al., "Validation of thoracic quantitative computed tomography as a method to measure bone mineral density", Calcif Tissue Int., 76(1), (Jan. 2005), 7-10.

World Health Organization, "Assessment of the fracture risk and its application to screening for postmeneopausal osteoporosis", Report No. WHO technical report series 843, Geneva:WHO, (1994), 1-129.

Yoganandan, B. S., et al., "Bone mineral density of human female cervical and lumbar spines from quantitative computed tomography", Spine, 31(1), (Jan. 2006), 73-76.

Bakhsheshi, H., et al., "Preview method for electron-beam CT scanning of the coronary arteries", Academic Radiology, vol. 7, N. 8, (Aug. 2000), 620-626.

Budoff, M.J., et al., "Trabecular bone mineral density measurement using thoracic and lumbar quantitative computed tomography", Academic Radiology, vol. 19, No. 2, (Feb. 2012), 179-183.

Hoffmann et al., "Vascular Calcification in ex Vivo Carotid Specimens: Precision and Accuracy of Measurements with Multi-Detector Row CT", Radiology, Nov. 2003, pp. 375-381.

* cited by examiner

Table 3A

Table 3B

METHOD FOR THORACIC VERTEBRAL BONE DENSITY MEASUREMENT BY THORACIC QUANTITATIVE COMPUTED TOMOGRAPHY

CROSS-REFERENCE TO RELATED APPLICATION

This application is a continuation application of U.S. patent application Ser. No. 14/806,472, filed Jul. 22, 2015, and entitled "METHOD FOR THORACIC VERTEBRAL BONE DENSITY MEASUREMENT BY THORACIC QUANTITATIVE COMPUTED TOMOGRAPHY", which is a continuation application of U.S. patent application Ser. No. 13/031,047, now U.S. Pat. No. 9,119,590, issued Sep. 1, 2015, and entitled "METHOD FOR THORACIC VERTEBRAL BONE DENSITY MEASUREMENT BY THORACIC QUANTITATIVE COMPUTED TOMOGRAPHY", which claims the priority benefit of U.S. Provisional Patent Application Ser. No. 61/305,698, filed Feb. 18, 2010, and entitled "METHOD FOR THORACIC VERTEBRAL BONE DENSITY MEASUREMENT BY THORACIC QUANTITATIVE COMPUTED TOMOGRAPHY", all of which are incorporated herein by reference in their entireties.

FIELD

A method for measurement of thoracic vertebral bone density.

BACKGROUND

Osteoporosis is the most common metabolic disorder of bone. The World Health Organization (WHO) estimates that 70 million people worldwide have osteoporosis. The annual worldwide incidence of hip fracture is 1.5 million, a number projected to grow to 2.6 million by 2025 and to 4.5 million by 2050. Bone strength is mostly dependent on its mineral content and therefore the measurement of bone mineral content is important to predict osteoporosis-related fractures. The most frequent site involved in fractures is the thoraco-lumbar junction, with mid-thoracic spine being the second most common site. The spine is the most sensitive site and is usually the first site to experience osteoporosis fractures. The bone turnover rate of the spinal trabecular bone is significantly higher than the cortical bone (the spinal trabecular bone remodeling rate is 5-10 times higher than the cortical bone).

Quantitative computed tomography (QCT) is a technique for three-dimensional bone mineral density (BMD) measurement. The bone density can be measured separately in the trabecular and cortical bone compartments. Therefore, thoracic quantitative computed tomography (TQCT) is an important technique for estimating and monitoring bone strength, especially in thoracic BMD measurement.

Cardiovascular diseases in general and coronary artery disease in particular remain the number one cause of death and disability in all industrialized and in many developing countries all over the world. In 2002, coronary artery disease, also referred to as coronary heart disease (CHD), caused 7.2 million deaths worldwide. Each year there are about 5.8 million new CHD cases, and about 40 million individuals with preventable CHD are alive today. The presence of calcium deposits in the coronary arteries has been well recognized as a marker of atherosclerotic coronary artery disease and gives independent incremental information, in addition to the traditional risk factors, in predicting cardiac events. Electron beam computed tomography (EBCT) has successfully been used to quantify plaque burden (by scoring calcification in the coronary arteries) over the past 20 years. Currently the cardiovascular CT scan is used widely to estimate calcium score and these scanners have obtained significantly higher temporal, special and contrast resolution with a significant decrease in radiation dosage using prospective triggering techniques. Current calcium scoring systems have a step-wise increase in scores that leads to decreased reproducibility using the Agatston score method. The most common current scoring system is one that uses the peak CT density, with a score of 1 applied for HU of 130-199, 2 for 200-299, 3 for 300-399 and 4 for 400 and greater. This impairs rescan reproducibility.

There is a significant positive association between BMD values obtained from the thoracic and lumbar spinal vertebrae ($r=0.93$ in female and $r=0.88$ in male). Even the cervical spine BMD is also reported to be significantly correlated with the lumbar BMD ($r=0.66$ to $0.87$). In this aspect, it has been shown that the TQCT with CAC scans give an adequate measure of BMD with a high degree of precision and reproducibility. Therefore, the thoracic cardiac scan is likely to be a useful ancillary assessment of bone mineral status in the population in general.

However, a significant difference in the BMD measurements found using the TQCT technique and the lumbar quantitative computed tomography (LQCT) technique has been reported (i.e., a different of 5.8-13.9%) and our study result (9.6% in female and 10.4% in male). This variation can be caused by various factors: such as scanner type, scan protocol, scan technique parameter, patient's age contribution, patient's status, etc. Bone density and loss rate have significant differences between lumbar and thoracic spines, therefore one cannot use current LQCT standard in TQCT measurement directly. The validating study is necessary to develop a method and reference standard by TQCT scan.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

DETAILED DESCRIPTION

Figure 1:
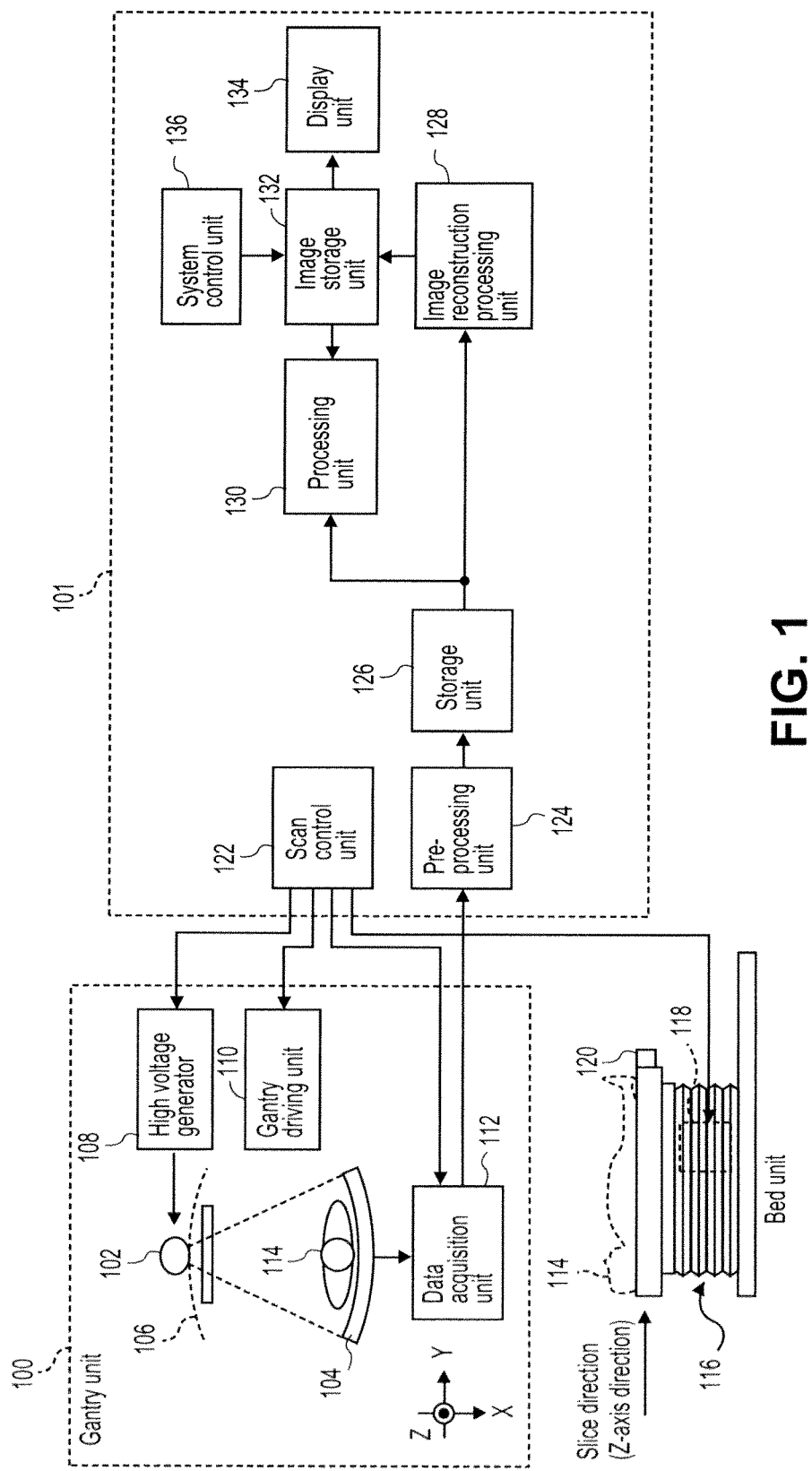
FIG. 1 illustrates a computed tomography scanner (CT) system.

A technique for determining bone mineral density (BMD) by using thoracic quantitative computed tomography (TQCT) with coronary artery calcium (CAC) scan is disclosed herein. As previously discussed, there are significant variations in lumbar and thoracic BMD of the same object due to the variation in scanner and scan protocol. The description provided herein discloses a technique for obtaining consistent BMD measurements regardless of the scanner used. The technique generally includes the use of a CT scanner to obtain a heart image of a desired coronary calcium scan. Data from the CT scanner is reconstructed into an image by a computing device. Beginning at the left main coronary artery level, the bone mineral density of three consecutive thoracic regions (3T) is measured and averaged to obtain thoracic bone mineral density. AT score measured by the TQCT can be used to estimate osteoporosis in the general population. A comparable T score with lumbar quantitative computed tomography (LQCT) in a subject who had a previous LQCT scan can be determined using the formulas disclosed herein. Similar T scores between TQCT and LQCT can be obtained using the formulas disclosed herein.

As previously discussed, current calcium scoring systems have a step-wise increase in scores that leads to decreased reproducibility using the Agatston score method. The most common current scoring system is one that uses the peak CT density, with a score of 1 applied for HU of 130-199, 2 for 200-299, 3 for 300-399 and 4 for 400 and greater. This impairs rescan reproducibility. For those reasons, the new scoring method disclosed herein uses the mean (not peak CTHU) CTHU/100 as the calcium lesion density scale. In particular, the score=area (mm2)×mean CTHU/100. At the time of coronary artery calcium (CAC) scan, the BMD of mid to lower thoracic spine can be measured simultaneously by using the TQCT technique.

A formula to translate the CTHU to $mg/cm^3$ may be generated and also used in CT CAC scan without calibration phantoms.

The CAC scan (row data) is completed with cardiovascular CT (electron beam CT-EBT or multiple detector row CT-MDCT) by using a snap shot protocol. By using this row data, a reconstructed image is completed with a field of view size (FOV) in 35-40 cm. In these images, the heart and 3-4 entire thoracic spine regions are included on mid to end thoracic segments. A computing device is used to measure the score of calcium burden and to estimate the risk possibility of coronary artery disease in the studied subject based on the images. A computing device may further be used to measure BMD from the images. The thoracic spine number and starting level covered by these CAC scans varies. The site of origin of left main (LM) coronary artery in all scans was at the level of T7, T8, T6 and T9 in about 50%, 30%, 19% and 1% cases respectively (computed from 300 cases with whole body scan). Three thoracic BMD measurements are made by the computing device starting at the level containing the left main (LM) coronary artery. The frequency consists of three thoracic series in 50%, 30%, 19% and 1% in four groups (6-8, 7-9, 8-10 and 9-11) respectively. The variation of measured BMD values within the 4 groups is about 1-2%.

The measurement of the thoracic vertebrae BMD was started at the slice level containing the left main coronary artery in all the CAC scans. The thickness of the region of interest (ROI) was 10 mm by Q5000 and 6 mm by NVivo. The center of ROI was located at the center of the vertebrae at a distance of 2-3 mm from the spinal cortical bone. The cortical bone, area with large venous vessel, islanded bone and calcifying herniated disk were excluded as much as possible from the ROI by using the free tracing protocol.

The mean BMD value of the three thoracic spines (3T) was calculated in all measurements. The 30 subgroups were formed based on two aging intervals in each gender (Table I).

The formula to calculate a predicted individual BMD (piBMD) in both genders was generated using the 30 subgroup data. The aging piBMD value from 30 to 90 years in general population was computed by using the formulas in each gender (Table 2).

The formula used to calculate predicted individual BMD (piBMD) in each gender was:

$$piBMD\ (mg/cm^3)=274.03-0.008\times age^2-1.304\times age\ (mg/cc)(R=0.99, P<0.001)\ \text{in females; and}$$

$$piBMD(mg/cm^3)=272.99-1.772\times age(R=0.99, P<0.001)\ \text{in males.}$$

The BMD of the 30 year old group (yBMD) in both genders was defined as a 'standard' for the young women and men. The common standard deviation (SD) of piBMD from 30 to 90 years in both gender were calculated.

The value of yBMD in the young group (30 years) was 221.9 $mg/cm^3$ in females and 215.2 $mg/cm^3$ in males. The mean standard deviation (SD) of both genders was 36 (in female) and 32 (in male) $mg/cm^3$. The T score formula by the TQCT measurement with the CAC scan was derived based on the young piBMD and the SD. T score=(individual mBMD−221.9)/36 in females; T score=(individual mBMD−215.2)/32 in males. The Z score of mBMD in general individual was calculated by the formula Z score=(individual mBMD−individual piBMD)/36 (or 32) in female or male respectively. In comparing the young group, a T score value of less than 2.5 is osteoporosis in any aging groups. The Z score value can be used to estimate osteoporosis in any aging group.

The measured thoracic BMD in each subject was significantly higher than the LQCT measurement (by 20.7% in females and 17.0% in males, P<0.001). A significant positive correlation was found to exist between the TQCT and the LQCT measurements (R>0.84, P<0.001). Based on the foregoing, it was determined that a modified formula for T score measurement by TQCT, which is comparable to the T score obtained by the LQCT, was needed.

The TQCT formulas can be used to measure BMD with the CAC scan directly, while in patients with a previous LQCT-BMD study, a modified TQCT formula can be used to obtain comparable T score value with prior study. Due to significant difference in thoracic and lumbar BMD value and loss rate per year, therefore, there is significant difference in T and Z score measured by TQCT and LQCT.

The QCT technique is a method to measure the bone CTHU and translate the CTHU to $mg/cm^3$. The translating function is performed by the plugs of calibration phantom. The other function of the calibration phantom is correcting the variation in inter-scans, inter-objects, inter-scan protocols commonly. The variation in inter-scan is more important than others. The techniques disclosed herein allow for the measurement of the thoracic spine CTHU followed by translation to mg/cm3 in a patient scan without the calibration phantom by using formulas.

FIG. 1 shows an arrangement of a computed tomography (CT) system. The CT system may be an X-ray CT device including gantry unit 100 and computing device 101. Although an X-ray CT device is described herein, it is further contemplated that the CT device may be an electron beam CT. Gantry unit 100 is designed to acquire projection data associated with a subject to be examined. Gantry unit 100 includes X-ray tube 102 and X-ray detector 104. X-ray detector 104 may be a 64-row multi-slice type detector (multi-row type detector) which covers the heart area. In other embodiments, a single-slice type detector (single-row detector) may be used as X-ray detector 104.

X-ray tube 102 and X-ray detector 104 may be mounted on a ring-shaped rotating frame 104 which is rotated/driven by gantry driving unit 110. In one embodiment, the rotation axis of rotating frame 104 is defined as the Z-axis. In a rotating coordinate system centered on the Z-axis, an axis perpendicular to the Z-axis which connects the focal point of X-ray tube 102 and the center of the detection surface of X-ray detector 104 is defined as the X-axis. The Y-axis is perpendicular to both the Z-axis and the X-axis.

An opening portion is formed in both the central portion of rotating frame 104 and the housing. In imaging operation, a subject 114 placed on top 120 of support unit 116 is inserted into the opening portion.

A high voltage generator 108 applies a tube voltage (high voltage) between the cathode and the anode of X-ray tube 102. The high voltage generator 108 also supplies a filament current to the filament of X-ray tube 102. X-rays are generated from X-ray tube 102 by the application of the tube voltage and the supply of the filament current.

X-ray detector 104 may have a plurality of X-ray detection elements. Data acquisition unit 112 generally called a DAS (Data Acquisition System) converts a signal output from X-ray detector 104 for each channel into a voltage signal, amplifies it, and further converts it into a digital signal. This data (also called pure raw data) is supplied to computing device 101 placed outside gantry 100. Computing device 101 may be any computing device capable of performing program execution such as a desktop, laptop, handheld, server or other similarly suitable type of wired or wireless computing device.

Pre-processing unit 124 of computing device 101 performs pre-processing such as sensitivity correction for the pure raw data output from data acquisition unit 112. The pre-processed pure raw data is called raw data or projection data. In this case, such data will be genetically called projection data.

Projection data may be stored in storage unit 126 while codes representing a view representing the rotation angle of X-ray tube 102 at the time of data acquisition, a row number, and the position of top 120 are associated with each other. Although this embodiment will exemplify a case wherein projection data obtained by helical scanning is processed, dynamic scanning is further contemplated.

Storage unit 126 may further include a machine-readable storage medium (or more specifically a computer-readable storage medium) on which is stored one or more sets of instructions embodying any one or more of the methodologies or functions described herein. During execution thereof by computing device 101, processing unit 130 may also constitute machine-readable storage media.

The machine-readable storage medium may also be used to store the instructions for determining thoracic vertebral bone mineral density. While the machine-readable storage medium is discussed in an exemplary embodiment to be a single medium, the term "machine-readable storage medium" and also "computer-readable medium" should be taken to include a single medium or multiple media (e.g., a centralized or distributed database, and/or associated caches and servers) that store the one or more sets of instructions. The terms "machine-readable storage medium" and "computer-readable medium" shall also be taken to include any medium that is capable of storing or encoding a set of instructions for execution by the machine and that cause the machine to perform any one or more of the methodologies of the present invention. The terms "machine-readable storage medium" and "computer-readable medium" shall accordingly be taken to include, but not be limited to, solid-state memories, and optical and magnetic media.

In addition to pre-processing unit 124 and storage unit 126, computing device 101 may include scan control unit 122, image reconstruction processing unit 128, processing unit 130, image storage unit 132, display unit 134 (The workstation to measure BMD of 3T and the coronary calcium score), and system control unit 136. Image reconstruction processing unit 128 performs image reconstruction on the basis of the projection data detected by X-ray detector 104. Image reconstruction processing unit 128 combines projection data of a plurality of heartbeats corresponding to a set cardiac phase to perform reconstruction, thereby displaying an image corresponding to the cardiac phase.

Figure 2:
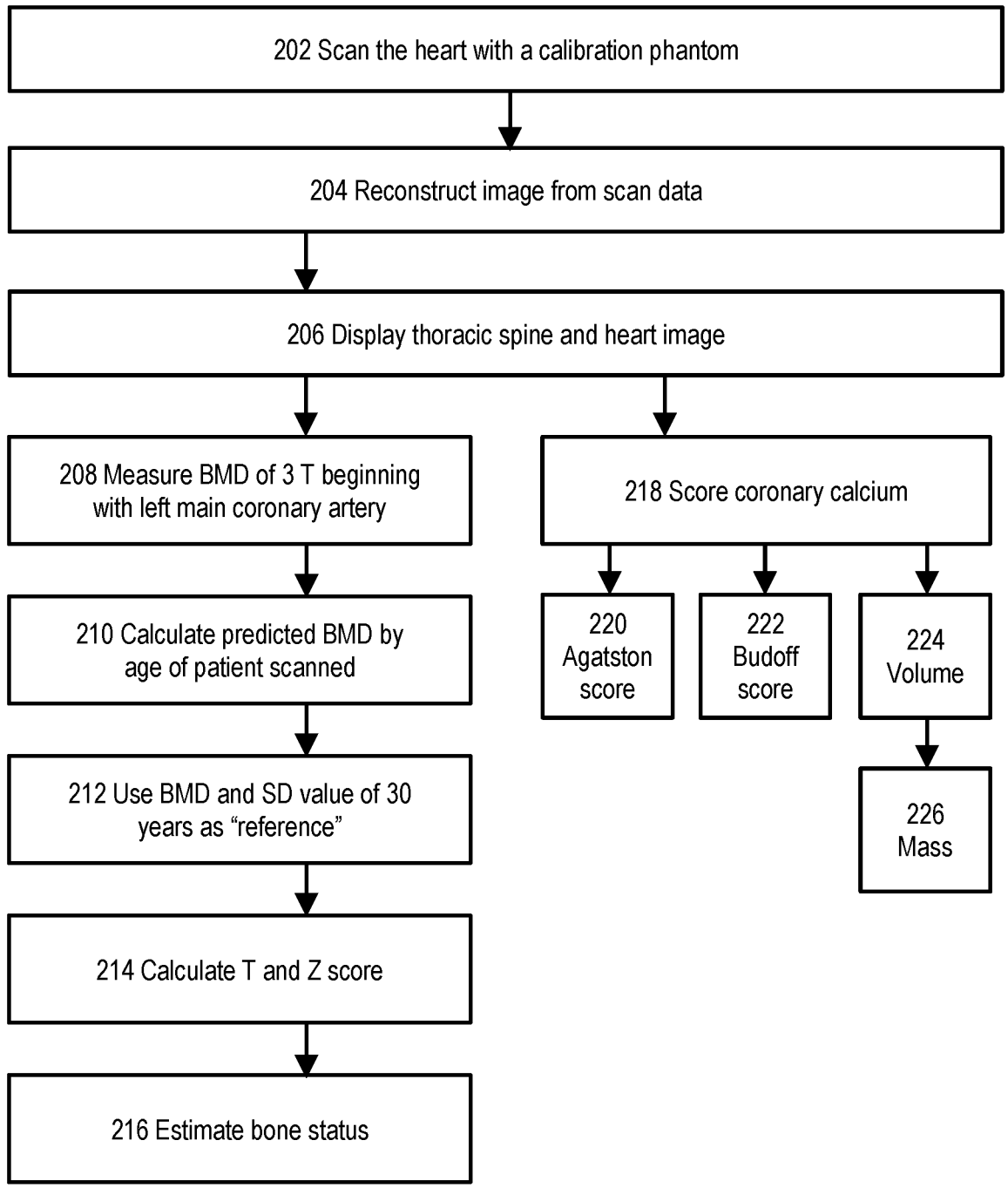
FIG. 2 is a flowchart illustrating one embodiment of a method for determining thoracic bone mineral density.

FIG. 2 is a flowchart illustrating one embodiment of a method for determining thoracic bone mineral density. In this embodiment, a scan of the heart is taken using a cardiovascular scanner capable of generating high-resolution images (block 202). Suitable scanners may include, but are not limited to, an electron beam tomography (EBT) scanner provided by GE !matron or other cardiovascular CT scanners provided by GE, Siemens, Toshiba and Philips and other manufacturers. Such scanners can freeze the heart motion with a prospective EKG trigger technique at mid diastole with a lower radiation dose and higher temporal resolution images.

After completing the heart scan, an axial image is reconstructed by using a field of view size in 35-40 cm for enclosing the heart and thoracic vertebrae in the same chest image (block 204). The axial images are transferred to a quantitative computed tomography (QCT) and cardiac workstation computing device. In some embodiments, the axial image is reconstructed at the computing device.

In some embodiments, the BMD of three thoracic spines 3T is determined (block 208) and/or a coronary artery calcium score is completed using the calculation disclosed herein (block 218).

Figure 4:
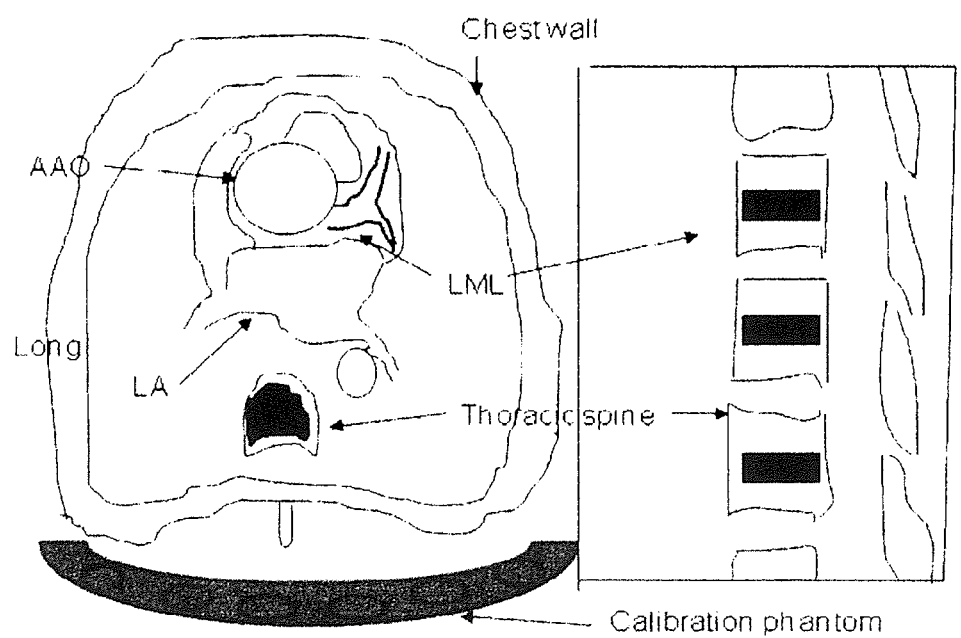
FIG. 4 illustrates an image displayed by a computing device of TQCT and LQCT.

The computing device may measure the BMD of three thoracic spines (3T) beginning at the left main coronary artery (block 208). Representatively, three kinds of images can be displayed in the QCT computing device, namely axial, sagittal and coronal images. The level of left main coronary artery is displayed by adjusting a height from sagittal or coronal images (FIG. 4 displays an axial image). Once the level of the left main coronary artery is found in the image, the cursor line is placed at the spine center (FIG. 4 displays a sagittal image). The center of the spine trabecular and plugs of calibration phantom can be found automatically by the QCT computing device. The CT Hounsfield unit (HU) and mg/cm3 can be displayed automatically by the computing device.

A first BMD measurement is taken at the spine level beginning at the main coronary artery. A second BMD measurement is taken at the spine following the spine level beginning at the main coronary artery. Finally, a third BMD measurement is taken at the spine following the first two spines. The thickness of the region of interest (ROI) is 6 mm or 10 mm and the center of ROI was located at the center of the vertebrae at a 2-3 mm distance from the spinal cortical bone. The cortical bone, area with large venous vessel, islanded bone and calcifying herniated disk were excluded as much as possible from the ROI by using the free tracing protocol.

The mean BMD value of (3T) the three measured thoracic spines in general population based on two aging intervals in each gender are listed in table 1:

TABLE 1

The profile of 30 aging groups in general population

| Age range (year) | Female | | | Male | | |
|---|---|---|---|---|---|---|
| | Mean age | Number | Mg/cm³ | Mean age | Number | Mg/cm³ |
| 30 | 30 | 42 | 221.9 | 30 | 53 | 215.2 |
| 31-32 | 31.5 | 42 | 217.3 | 31.5 | 51 | 216.6 |
| 33-34 | 33.5 | 38 | 215.7 | 33.5 | 55 | 215.1 |
| 35-36 | 35.5 | 35 | 215.7 | 35.6 | 66 | 210.0 |
| 37-38 | 37.5 | 39 | 213.0 | 37.5 | 58 | 207.1 |
| 39-40 | 39.5 | 42 | 211.9 | 39.6 | 99 | 206.0 |
| 41-42 | 41.4 | 56 | 209.9 | 41.6 | 119 | 206.8 |
| 43-44 | 43.6 | 89 | 208.5 | 43.5 | 152 | 200.2 |
| 45-46 | 45.5 | 118 | 207.6 | 45.5 | 197 | 193.2 |
| 47-48 | 47.6 | 128 | 199.2 | 47.6 | 234 | 188.6 |
| 49-50 | 49.6 | 160 | 197.2 | 49.5 | 286 | 184.5 |
| 51-52 | 51.6 | 213 | 190.5 | 51.5 | 298 | 176.9 |
| 53-54 | 53.5 | 242 | 181.1 | 53.5 | 364 | 176.1 |
| 55-56 | 55.6 | 277 | 174.3 | 55.5 | 374 | 173.2 |
| 57-58 | 57.5 | 252 | 166.6 | 57.5 | 354 | 165.8 |
| 59-60 | 59.5 | 201 | 165.1 | 59.5 | 351 | 165.9 |
| 61-62 | 61.5 | 264 | 157.4 | 61.5 | 281 | 162.5 |
| 63-64 | 63.5 | 263 | 154.5 | 63.5 | 283 | 160.3 |
| 65-66 | 65.5 | 257 | 153.5 | 65.5 | 303 | 154.7 |
| 67-68 | 67.5 | 222 | 148.4 | 67.5 | 251 | 154.7 |
| 69-70 | 69.5 | 196 | 143.3 | 69.5 | 256 | 151.6 |
| 71-72 | 71.4 | 240 | 137.3 | 71.6 | 189 | 148.1 |
| 73-74 | 73.5 | 168 | 131.8 | 73.5 | 189 | 144.3 |
| 75-76 | 75.5 | 149 | 126.1 | 75.5 | 165 | 137.2 |
| 77-78 | 77.5 | 111 | 125.3 | 77.6 | 137 | 133.4 |
| 79-80 | 79.5 | 97 | 117.2 | 79.4 | 103 | 133.5 |
| 81-82 | 81.5 | 78 | 109.4 | 81.4 | 68 | 132.6 |
| 83-84 | 83.6 | 52 | 108.5 | 83.5 | 61 | 124.9 |
| 85-86 | 85.5 | 31 | 109.7 | 85.6 | 44 | 120.5 |
| 87-90 | 88.4 | 24 | 102.8 | 88.9 | 13 | 116.0 |

Based on the measured BMD data, the predicted general individual BMD formula is computed (piBMD) (block 210). The formula used to calculate aging predicted BMD (piBMD) in each gender may be: piBMD (mg/cm³) =274.03−0.008×age²−1.304×age (mg/cc) (R=0.99, P<0.001) in females; =272.99−1.772×age (R=0.99, P<0.001) in males. The piBMD in general population in each gender is computed and listed in Table 2 below.

TABLE 2

The profile of predicted BMD (piBMD, mg/cm³) in the general population

| Age(year2) | Female | male | Age | Female | male |
|---|---|---|---|---|---|
| 30 | 227.6 | 219.8 | 61 | 164.3 | 164.9 |
| 31 | 225.8 | 218.0 | 62 | 162.0 | 163.1 |
| 32 | 224.0 | 216.3 | 63 | 159.7 | 161.3 |
| 33 | 222.2 | 214.5 | 64 | 157.4 | 159.6 |
| 34 | 220.3 | 212.7 | 65 | 155.0 | 157.8 |
| 35 | 218.5 | 210.9 | 66 | 152.7 | 156.0 |
| 36 | 216.6 | 209.6 | 67 | 150.3 | 154.3 |
| 37 | 214.7 | 207.4 | 68 | 147.9 | 152.5 |
| 38 | 212.8 | 205.6 | 69 | 144.5 | 150.7 |
| 39 | 210.8 | 203.8 | 70 | 143.0 | 148.9 |
| 40 | 208.9 | 202.1 | 71 | 140.6 | 147.2 |
| 41 | 206.9 | 200.3 | 72 | 138.1 | 145.4 |
| 42 | 205.0 | 198.5 | 73 | 135.7 | 143.6 |
| 43 | 203.0 | 196.7 | 74 | 133.2 | 141.9 |
| 44 | 201.0 | 195.0 | 75 | 130.7 | 140.1 |
| 45 | 198.9 | 193.2 | 76 | 128.1 | 138.3 |
| 46 | 196.9 | 191.5 | 77 | 125.6 | 136.5 |
| 47 | 194.8 | 189.7 | 78 | 123.0 | 134.8 |
| 48 | 192.8 | 187.9 | 79 | 120.4 | 132.9 |

TABLE 2-continued

The profile of predicted BMD (piBMD, mg/cm³) in the general population

| Age(year2) | Female | male | Age | Female | male |
|---|---|---|---|---|---|
| 49 | 190.7 | 186.1 | 80 | 117.9 | 131.2 |
| 50 | 188.6 | 184.4 | 81 | 115.2 | 129.5 |
| 51 | 186.4 | 182.6 | 82 | 112.6 | 127.7 |
| 52 | 184.3 | 180.8 | 83 | 110.0 | 125.9 |
| 53 | 182.2 | 179.1 | 84 | 107.3 | 124.1 |
| 54 | 180.0 | 177.3 | 85 | 104.7 | 122.4 |
| 55 | 177.8 | 175.5 | 86 | 102.0 | 120.6 |
| 56 | 175.6 | 173.7 | 87 | 99.3 | 118.8 |
| 57 | 173.4 | 171.9 | 88 | 96.5 | 117.1 |
| 58 | 171.1 | 170.2 | 89 | 93.8 | 115.3 |
| 59 | 168.9 | 168.4 | 90 | 91.4 | 113.5 |
| 60 | 166.6 | 166.7 | 30-90 | 164.1 | 166.7 |

In T score calculating, the mBMD of the 30 year old group in both genders was defined as a 'standard' for the young women and men. In Z score measuring, the predicted individual BMD (piBMD) value of each aging group is the 'reference' value. The standard deviation (SD) of piBMD from 30-90 years in both gender groups was calculated, and adjusted (to obtain similar T scores to that obtained by scanning the lumbar region), as a factor to calculate T and Z score.

The value of yBMD in the young sample group (30 years) was calculated (block 212). The yBMD value was found to be 221.9 in females and 215.2 mg/cm³ in males. The standard deviation (SD) of both gender groups was 36 (in female) and 32 (in male) mg/cm3.

Figure 6A:
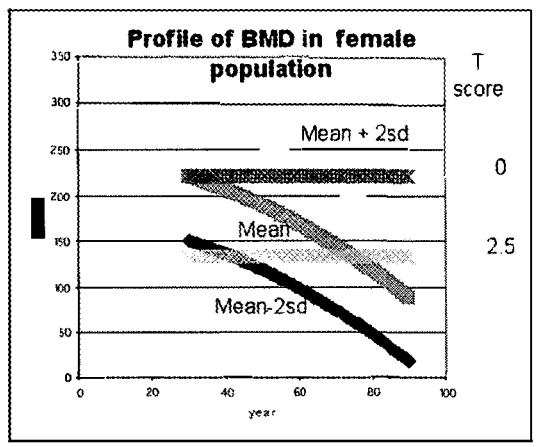
FIG. 6A illustrates a profile of bone mineral density in females.
Figure 6B:
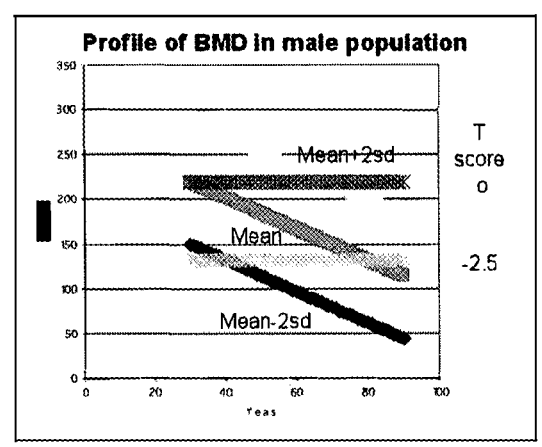
FIG. 6B illustrates a profile of bone mineral density in males.

Next, T and Z scores were calculated (block 214). The T score is a comparison of a person's yBMD to that of a healthy 30 year old of the same sex and ethnicity. The Z score is a number of standard deviations a patient's BMD differs from the average BMD of others of their same age, sex and ethnicity. The T score formula for the TQCT measurement with the CAC scan was derived based on the ymBMD and the SD. In one embodiment, T score=(individual mBMD−221.9)/36 in females; T score=(individual mBMD−215.2)/32 in males. The Z score of mBMD in a general individual was calculated by the formula Z score= (individual mBMD−piBMD)/36 (or 32) in female and male respectively. From the T and Z scores calculated, the bone status of the subject is estimated (block 216). Representatively, comparing the young group, a T score value of less than −2.5 is considered osteoporosis in any aging groups and a T score of less than −1 is considered osteopenia. The Z score value can be used to estimate osteoporosis in any aging group. These results are illustrated by Table 3A and Table 3B shown in FIG. 6A and FIG. 6B, respectively.

Figure 3:
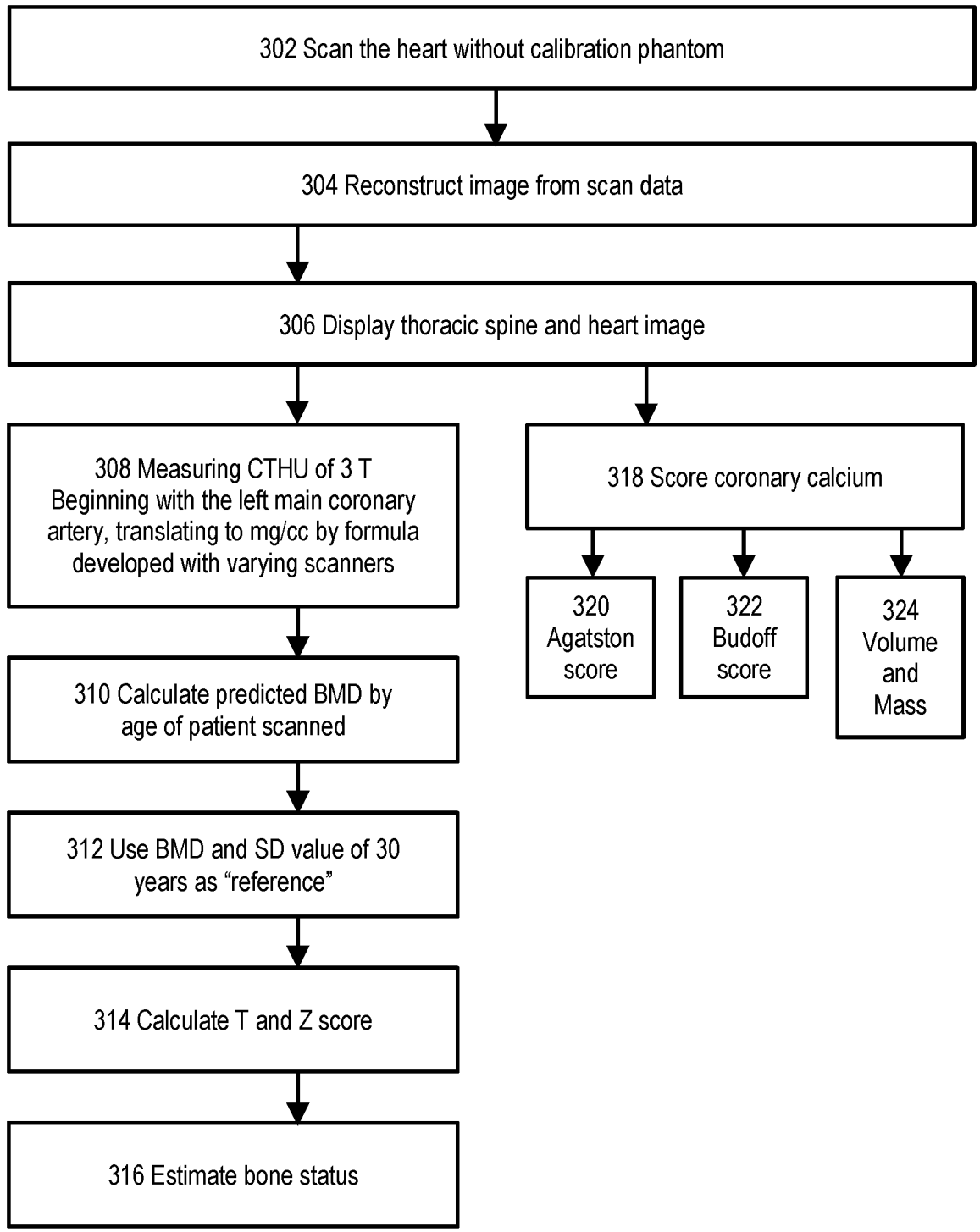
FIG. 3 is a flowchart illustrating one embodiment of a method for determining thoracic bone mineral density.

The modified formulas were generated in both genders, which are used to translate the TQCT value to closed LQCT value in patients with prior LQCT studies and used in connection with the method illustrated in FIGS. 2 and 3. LQCT T score=0.8789×TQCT T score+0.2688 in females; LQCT T score=0.8139×TQCT score+11.822 in males As previously discussed, coronary calcium score may also be determined (block 218). In some embodiments, the traditional Agatston score method is used (block 220). Using the Agatston formula, score=calcium lesion area mm²×peak density scale (CTHU, in 1,2,3, and 4),1-CTHU 130-200,2-CTHU 201-300,3-CTHU 301-400and 4-CTHU>400.

Volume(mm³)=Area(mm²)×thickness(mm)

In some embodiments, a Budoff score method is used (block 222). The Budoff score method refers to the novel score method disclosed herein. The Agatston score is step-wise, which can reduce the rescan, interscanner and inter-individaul reproducibility. The peak CTHU cannot represent the total lesion density optimally. For those reasons, a new scoring system, the Budoff scoring method, was created. In this scoring system, the mean (not peak CTHU) CTHU/100 is used as the calcium lesion density scale, The Budoff score=area (mm$^2$)×mean CTHU/100, or CAC foci volume/ slice thickness×mean CTHU/100.

In some embodiments, a calcium mass calculation is performed (blocks 224, 226). The calcium lesion mass (mg) formula is:

volume(mm$^3$)×density of CaHA(mg/mm$^3$)

the density represented by calibration factor.

In traditional CAC foci mass measurement, the density value is estimated, not calculated with use of a calibration phantom. Others used the formula induced by calibration phantom. In this score system, the calibration factor (CF, mg/cc/CTHU) of calibration phantom plugs (displayed on FIG. 5) is used to translate the CTHU to mg/mm$^3$ of calcium foci, like BMD measurement, a given Foci Mass=CF× volume (mm$^3$).

For patients with a traditional calibration phantom, the BMD formula is CTHU×AF, calculated from the phantom plugs or by the ratio of CTHU/mg/cc (BMD=CTHU/ratio).

FIG. 3 is a flowchart illustrating one embodiment of a method for determining thoracic bone mineral density. The method illustrated in FIG. 3 is similar to the method disclosed in reference to FIG. 2, except that the scan is performed without a calibration phantom (block 304). An image is reconstructed from the scan data (block 304). Once reconstructed, the thoracic spine and heart image are displayed (block 306).

In some embodiments, the BMD of three thoracic spines 3T is determined (block 308) and/or a coronary artery calcium score is completed using the calculation disclosed herein (block 318).

The computed tomography Hounsfield unit (CTHU) of three thoracic spines (3T) is measured (block 308). In this aspect, a first spine CTHU measurement is taken at the spine level beginning at the main coronary artery. A second CTHU measurement is taken at the spine level beginning at the main coronary artery. Finally, a third CTHU measurement is taken at the spine following the first two spines. Next, CTHU is translated to mg/cm3 (block 310) by the ratio of CTHU/mg/cc displayed on table 5 (if using a new calibration phantom, see FIG. 5) or by the ratio of phantom plug with 150 mg/cc (or mean of 100-200 mg/cc). According to the technique disclosed herein, the thoracic spine CTHU can be measured by a variety of scanners then translated to mg/cm$^3$ In EBT scanner, the location of fixed X-ray target is under table with range angle of 210°, this design inducing more X-ray dose receipted by phantom (reference) area and significantly higher CTHU than the spine. Therefore, the BMD by EBT is lower than MDCT in the same individual. One hundred and fifty six cases who underwent CAC study by both EBT and 64-row detector GE scanner (VCT, GE Healthcare, Milwaukee, Wis.) on the same day were used to compare and normalize the BMD values between scanners. In comparing the mBMD value of both scanners (EBT and MDCT-GE64), there was an average underestimation of 18% as measured by EBT as compared to the GE scanner. Currently, most QCT and cardiac studies are performed using MDCT scanners. To normalize the EBT C300 and C150 scanner) to the MDCT, we used the following formula (Y=1.082 X+12.5, R=0.97). In EBT eSpeed scanner, the translating Formula is Y=1.1 X.

Formulas for translating the CTHU values for each of the different types of scanners are listed below. One can use the formulas or use calibrating factor (CF) to calculate BMD (BMD=spinal HU×CF) or CAC mass score (=CAC foci mean HU×CF) on phantom less CAC images.

C100: y=0.9+13.11, R=0.97, n=344, 130 kVp, Calibrating factor=0.99 eSpeed: Equivalent value with GE scanner=0.98×HU (by eSpeed scanner)+2.86 (mg/cm$^3$), R=0.98, n=330, 130 kVp, Calibrating factor=0.86

C150: Equivalent value with GE scanner=0.95×HU (by C150 scanner)+7.34 (mg/cm$^3$), R=0.99, n=3701, 130 kVp, Calibrating factor=0.84

C300: Equivalent value with GE scanner=0.9×HU (by C300 scanner)+14.3(mg/cm$^3$), R=0.97, n=1959, 130 kVp, Calibrating factor=0.83

For multiple detector CT scanners, the Formula, calibrating factor was listed on Table 4:

TABLE 4

Calibrating factor and calculation formula with CTHU in various MDCT scanners

| Scaner and ditector | NO | CF Formula | R value | kVP |
|---|---|---|---|---|
| Philips 256 | 186 | 0.874 y = 0.855x + 3.088 | R$^2$ = 0.965 | 120 |
| Philips 64 | 200 | 1.006 y = 0.888x + 2.959 | R$^2$ = 0.994 | 120 |
| Philips 16 | 210 | 0.982 y = 0.937x + 5.570 | R$^2$ = 0.993 | 140 |
| Toshiba 320 | 200 | 0.906 y = 0.929x − 4.718 | R$^2$ = 0.995 | 135 |
| Toshiba 64 | 170 | 0.914 y = 0.904x | R$^2$ = 0.978 | 135 |
| Toshiba 16 | 200 | 0.973 y = 0.983x + 4.065 | R$^2$ = 0.986 | 135 |
| HEHD 64 | 194 | 0.91 y = 0.860x + 7.588 | R$^2$ = 0.991 | 120 |
| Ge 64 | 185 | 0.923 y = 0.889x + 5.648 | R$^2$ = 0.991 | 120 |
| Ge 16 | 244 | 0.804 y = 0.829x − 1.859 | R$^2$ = 0.992 | 120 |
| Siemens Dual | 195 | 1.031 y = 0.967x + 7.772 | R$^2$ = 0.952 | 120 |
| Siemens 64 | 216 | 0.954 y = 0.934x + 5.723 | R$^2$ = 0.989 | 120 |
| Siemens 16 | 180 | 0.975 y = 0.962x + 2.676 | R$^2$ = 0.995 | 140 |

The value of yBMD in the young sample group (30 years) was calculated (block 312). The yBMD value was found to be 221.9 in females and 215.2 mg/cm$^3$ in males. The standard deviation (SD) of both gender groups was 36 (in female) and 32 (in male) mg/cm3

Next, T and Z scores were calculated (block 314). The T score is a comparison of a person's yBMD to that of a healthy 30 year old of the same sex and ethnicity. The Z score is a number of standard deviations a patient's BMD differs from the average. BMD of others of their same age, sex and ethnicity. The T score formula for the TQCT measurement with the CAC scan was derived based on the ymBMD and the SD. In one embodiment, T score=(individual mBMD−221.9)/36 in females; T score=(individual mBMD−215.2)/32 in males. The Z score of mBMD in a general individual was calculated by the formula Z score= (individual mBMD−piBMD)/36 (or 32) in female and male respectively. From the T and Z scores calculated, the bone status of the subject is estimated (block 316). Representatively, comparing the young group, a T score value of less than −2.5 is considered osteoporosis in any aging groups and a T score of less than −1 is considered osteopenia. The Z score value can be used to estimate osteoporosis in any aging group.

As previously discussed, coronary calcium score may also be determined (block 318). The Agatston score method (block 320), Budoff score method 322 and/or calcium mass calculation (block 324) may be used as previously discussed in reference to FIG. 2.

FIG. 4 illustrates an image displayed by a computing device (workstation computer). The left and right panels of FIG. 4 illustrate an axial image and a sagittal image. From this image, BMD measurements as described herein can be made.

Figure 5:
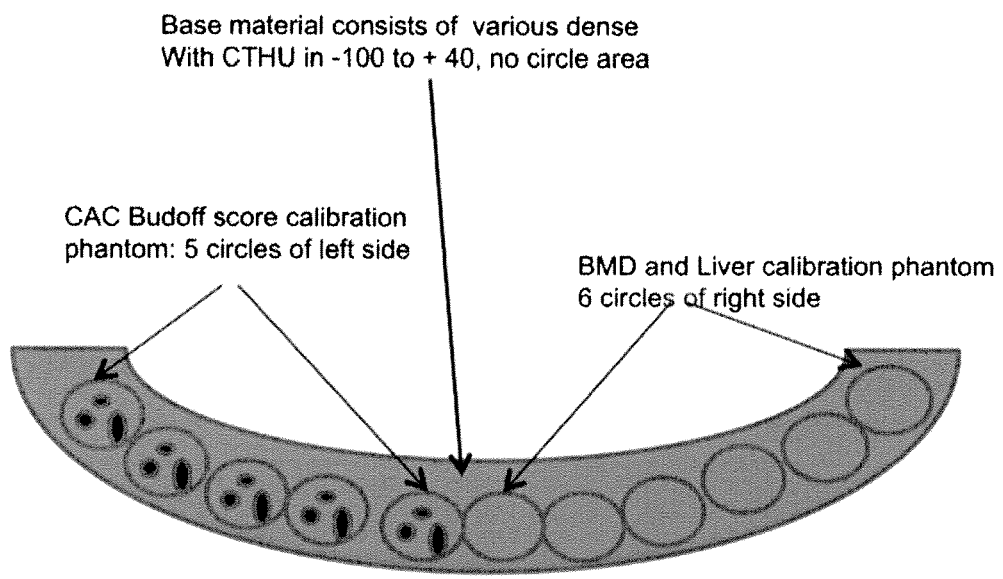
FIG. 5 illustrates one embodiment of calibration phantom used to translate CTHU to BMD (mg/cc), to calculate CAC mass score and calibrate CAC score.

FIG. 5 illustrates a calibration phantom with 11 plugs containing calcium hydroxyapatite (CaHA) in various density. Left 5 circles are CAC Budoff score calibration phantom: Consists of various dense (130,200,300,400 and 600 mg/cm$^3$ of CaHA or Human bone tissue) with the Agatston value in 2.5, 7.5 and 50 closely. Right 6 circles are BMD and Liver calibration phantom: the BMD phantom consists of various dense of plugs containing human nature bone or CaHA with 0, 50,100,200,400 mg/cm$^3$ The liver phantom with a liver dense (60 CTHU measured by GE 64 scanner with 120 kVp and 50 mAs) with O CaHA, made by human soft tissue or other material. Currently two kinds of calibration phantoms are commonly used: phantom 1 has three plugs containing CaHA in 0, 75 and 150 mg/cm$^3$ and 12 inches in length and phantom 2 has 4 plugs containing CaHA in 0, 50, 100,200 mg/cm$^3$ respectively (Image analysis, Columbia, Ky.).

To perform LQCT studies, an image with a calibration phantom under patient's back is scanned, the plugs densities (CTHU) are detected by computer, and the formula to translate CTHU to mg/cc is computed individually. Two shortcomings of commonly used calibration phantoms are: (1) the range of phantom plugs containing CaHA does not cover the common BMD values found in the thoracic spine; and (2) the ratio of HU/mg/cc varies significantly throughout the length of the spine. Theoretically, the optimal translation method is using the ratio (HU/mg/cc) of a given phantom plug to correct the spine BMD that closed in HU with used plug.

To design an optimal plug size of calibration phantom, we have obtained the BMD contribution of thoracic spine vertebrae in 9807 general population undergoing CAC scans displaying in following Table 5.

TABLE 5

The distribution of general population
Distribution of 9807 population
22-90 ys

| mg/cc | no | Percent (%) | Phantom |
|---|---|---|---|
| 20-50 | 22 | 0.2243 | 30 |
| 51-100 | 673 | 6.8624 | 75 |
| 101-150 | 3148 | 32.1 | 125 |
| 150-200 | 3730 | 38.034 | 175 |
| 201-250 | 1783 | 18.181 | 225 |
| 251-300 | 392 | 3.9971 | 300 |
| 301-350 | 54 | 0.5506 | |
| >350 | 5 | 0.051 | |
| sum | 9807 | 100 | |

According to these values, the 6 plugs can be used to make a new phantom, there are plugs containing the various concentration of CaHA displayed in Table 5. The plugs containing 60 mg/cc CaHA can be used to calibrate the liver. Overall, 99% of thoracic BMD range can be covered by using the new calibration phantom displayed in FIG. 5. The benefits of using this new calibration phantom are: (1) Covering 99% of BMD range of thoracic vertebrae; and (2) Decrease the calculation error by use of a formula (3). Can be used to calculate CAC fuci mass score and calibrate CAC score.

In some embodiments, a new computer system for BMD measurement is contemplated. The computer system may include a computer program implemented by a workstation BMD computer. For the CT image with a new calibration phantom, the program may be used to perform the following operations:

1. Detect the CTHU of calibration phantom plugs and calculating the ratio of HU/mg/cc or CF (mg/cc/CTHU),
2. Detect the CTHU of given thoracic spine,
3. Translate CTHU to mg/cc of this spine by using the ratio of plug that is closest to the density of the spine itself. For example: If the CTHU of a given thoracic spine is 63, the CTHU is 85 at plug containing CaHA in 75 mg/cc, that is close with the 63 hu, the ratio 1.133 (85/75) is 1.333, therefore 63/1.133=55.6 mg/cc in this spine. Or using CF (CTHU×CF)

In some embodiments, the computer program and a workstation BMD computer can be used for imaging with a traditional calibration phantom (0, 75, 150 mg/cc) as follows:

1. Detect the CTHU of Plug with 150 mg/cc CaHA and calculate ratio (150-ratio),
2. Obtain the ratio of a given spine (G-ratio), G-ratio=150-ratio+D (difference between a given spine and plug of 150 mg/cc). The G-ratio can be found from Tables 5 and 6.
3. Translate HU to mg/cc at a Given spine, BMD mg/cc=CTHU/G-ratio, or CTHU×CF.

In other embodiments, the computer program and workstation BMD computer may be used in patients with a traditional phantom (0, 50, 100 and 200 mg/cc) as follows:

1. Detect the CTHU of Plug with 100 and 200 mg/cc CaHA and calculate the 150-ratio (150-ratio, =mean ratio of 100 and 200-ratio),
2. Obtain the ratio of a given spine (G-ratio), G-ratio=150-ratio+D value (difference between a given spine and plug of 150 mg/cc). The G-ratio can be find from following table, displayed on [0068] and [0069].
3. Translate HU to mg/cc at a Given spine, BMD mg/cc=CTHU/G-ratio, or CTHU×CF.

The analysis is the ratio of different density of the spine in 22,269 patients to establish norms for different scanners for thoracic vertebra. From this data, the optimal calibration plug size and calibration method for a computer system is derived. In Table 6, the value of >400 mg/cc were measured from cortical bone or calcium foci.

TABLE 6

Ratio of CTHU/mg/cc in varying BMD range and scanners

| bone- hu/mg/cc | C100 | eSpeed | Philips Phantom | C300 ratio ratio | ge16 Ratio Ratio | C150 ratio ratio | Ge64 ratio ratio | Simens ratio ratio | Toshiba ratio ratio |
|---|---|---|---|---|---|---|---|---|---|
| 20-50 mg/cc | | | 1.113 | 1.175 | 1.224 | 1.309 | 0.845 | 0.931 | 0.945 |
| 51-100 | | | 1.134 | 1.2 | 1.22 | 1.217 | 0.845 | 1.0016 | 0.965 |
| 101-150 | | | 1.138 | 1.202 | 1.211 | 1.188 | 1.0345 | 1.0317 | 1.006 |
| 150-200 | | | 1.146 | 1.202 | 1.211 | 1.171 | 1.0438 | 1.0427 | 1.013 |
| 201-250 | | | | 1.202 | 1.211 | 1.16 | 1.0598 | 1.0434 | 1.014 |
| 251-300 | | | | 1.202 | 1.211 | 1.138 | 1.073 | 1.0443 | 1.014 |
| 301-350 | | | | 1.208 | 1.211 | 1.132 | 1.092 | 1.0495 | 1.019 |
| 351-400 | | | | 1.211 | 1.211 | 1.1 | 1.117 | 1.061 | 1.021 |
| 401-500 | | | | 1.211 | 1.211 | 1.1 | 1.119 | 1.07 | 1.023 |
| 501-600 | | | | 1.211 | 1.211 | 1.1 | 1.121 | 1.08 | 1.04 |
| 601-700 | | | | 1.211 | 1.211 | 1.1 | 1.121 | 1.091 | 1.04 |
| >701 | | | | 1.211 | 1.211 | 1.1 | 1.121 | 1.099 | 1.04 |
| sum | 1.01 | 1.1 | 1.133 | 1.2 | 1.21 | 1.21 | 1.01 | 1.01 | 0.99 |
| number | 344 | 330 | 54 | 2450 | 2401 | 3200 | 7940 | 4200 | 1350 |

D values of given spine with varying range of BMD and scanners were obtained from Table 6 (D value=a G-ratio–C150-ratio), C150-ratio is the value of ratio in spine with the dense in 150 mg/cc of phantom plug.

TABLE 7

D values (a G-ratio – C150-ratio) in varying BMD range and scanners

| mg/cc | c300 Ratio D value | GE16 Ratio D value | C150 Ratio D value | ge64 Ratio D value | Simens Ratio D value | Toshiba Ratio D value | philip Ratio D value |
|---|---|---|---|---|---|---|---|
| 20-50 | −0.03 | 0.013 | 0.128 | −0.1948 | −0.1038 | −0.068 | −0.025 |
| 51-100 | −0.002 | 0.009 | 0.036 | −0.1948 | −0.0332 | −0.049 | 0.004 |
| 101-200 (150) | 0 | 0 | 0 | 0 | 0 | 0 | 0 |
| 201-250 | 0 | 0 | −0.021 | 0.02 | 0.0086 | 0.007 | 0.008 |
| 251-300 | 0 | 0 | −0.043 | 0.0332 | 0.0095 | 0.007 | |
| 301-350 | 0 | 0 | −0.049 | 0.0522 | 0.0147 | 0.012 | |
| 351-400 | 0.006 | 0 | −0.081 | 0.0772 | 0.0262 | 0.014 | |
| 401-500 | 0.009 | 0 | −0.081 | 0.0792 | 0.0352 | 0.016 | |
| 501-600 | 0.009 | 0 | −0.081 | 0.0812 | 0.0452 | 0.033 | |
| 601-700 | 0.009 | 0 | −0.081 | 0.0812 | 0.0562 | 0.033 | |
| >701 | 0.009 | 0 | −0.081 | 0.0812 | 0.0642 | 0.033 | |

In some embodiments, the computer program and a workstation BMD computer may be used in patients without calibration phantom. The system can detect the CTHU of mid trabecula of 3T in 6 mm thickness automatically. The system then translates CTHU to mg/cc by the ratio in varying scanners: CTHU/G-ratio, displayed on Table 6, or by formulas previously discussed.

A device, such as device 101, for performing the operations herein may be specially constructed for the required purposes or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, Flash memory devices including universal serial bus (USB) storage devices (e.g., USB key devices) or any type of media suitable for storing electronic instructions, each of which may be coupled to a computer system bus.

The algorithms and displays presented herein are not inherently related to any particular computer or other apparatus. Various general purpose systems may be used with programs in accordance with the teachings herein or it may prove convenient to construct a more specialized device to perform the described method. In addition, the invention is not described with reference to any particular programming language. It will be appreciated that a variety of programming languages may be used to implement the teachings of the invention as described herein.

A computer readable medium includes any mechanism for storing information in a form readable by a computer. For example, a computer readable medium includes read only memory ("ROM"), random access memory ("RAM"), magnetic disk storage media, optical storage media, flash memory devices or other type of machine-accessible storage media.

In the preceding detailed description, specific embodiments are described. It will, however, be evident that various modifications and changes may be made thereto without departing from the broader spirit and scope of the claims. The specification and drawings are, accordingly, is to be regarded in an illustrative rather than restrictive sense.

What is claimed is:

1. A method for determining bone mineral density (BMD) using quantitative computed tomography (QCT) without a calibration phantom, the method comprising:
    obtaining image data representing a heart from a scan performed by a computed tomography (CT) scanner;
    using the image data, calculating a BMD at two or more spine levels by:
        identifying, using a computer, a spine level at a position corresponding to a site of origin of an identified left main coronary artery; and
        calculating, using the computer, a BMD based on computed tomography Hounsfield Unit (CTHU) values computed from a portion of the image data associated with the spine level at the position corresponding to the site of origin of the left main coronary artery and CTHU values computed from portions of the image data associated with one or more additional, consecutive, and different spine levels; and
    determining, using the computer, a thoracic trabecular BMD measurement based on the BMD calculations at the spine level at the position corresponding to the site of origin of the left main coronary artery and the one or more additional, consecutive, and different spine levels, wherein the thoracic trabecular BMD measurement is normalized to a BMD determined by a multiple detector computed tomography (MDCT) technique using a translation formula based on at least one prior MDCT measurement such that the thoracic trabecular BMD measurement is determined without a calibration phantom, wherein the translation formula used to normalize the thoracic trabecular BMD measurement to the BMD determined by the multiple detector computed tomography (MDCT) technique includes two different constants, each of which are representative of a different quantitative factor associated with normalization of BMD, and constant for a given CT scanner and tissue density.

2. The method of claim 1, wherein the image data comprises CT image data representing the heart and a thoracic spine.

3. The method of claim 1, wherein the image data comprises CT image data representing the left main coronary artery and at least three thoracic spine levels, wherein a first one of the at least three thoracic spine levels is the spine level at the position corresponding to the site of origin of the left main coronary artery.

4. The method of claim 1, wherein the CT image data is obtained at a temporal resolution of less than 400 milliseconds/rotation.

5. The method of claim 1, wherein the translation formula used to normalize the thoracic trabecular BMD measurement to the BMD determined by the multiple detector computed tomography (MDCT) technique is of the form
BMD=m*[BMD(CT)]+b, where BMD(CT) refers to the determined thoracic trabecular BMD measurement and each of m and b are the different constants which are representative of different quantitative factors associated with normalization of BMD, and constant for a given CT scanner and tissue density.

6. The method of claim 5, wherein the constant m is different for different CT scanner models for a given tissue density, and m is determined for a specific CT scanner model.

7. A system configured for determining bone mineral density (BMD) using quantitative computed tomography without a calibration phantom, the system comprising:
one or more processors configured by computer readable instructions to:
obtain image data representing a heart from a scan performed by a computed tomography (CT) scanner;
using the image data, calculate a BMD at two or more spine levels by:
identifying a spine level at a position corresponding to a site of origin of an identified left main coronary artery in the image data; and
calculating a BMD based on computed tomography Hounsfield Unit (CTHU) values computed from a portion of the image data associated with the spine level at the position corresponding to the site of origin of the left main coronary artery and CTHU values computed from portions of the image data associated with one or more additional, consecutive, and different spine levels; and
determine a thoracic trabecular BMD measurement based on the BMD calculations for the spine level at the position corresponding to the site of origin of the left main coronary artery and the one or more additional, consecutive, and different spine levels, wherein the thoracic trabecular BMD measurement is normalized to a BMD determined by a multiple detector computed tomography (MDCT) technique using a translation formula based on at least one prior MDCT measurement such that the thoracic trabecular BMD measurement is determined without a calibration phantom;

wherein the translation formula used to normalize the thoracic trabecular BMD measurement to the BMD determined by the multiple detector computed tomography (MDCT) technique includes two different constants, each of which are representative of a different quantitative factor associated with normalization of BMD, and constant for a given CT scanner and tissue density.

8. The system of claim 7, wherein the translation formula used to normalize the thoracic trabecular BMD measurement to the BMD determined by the multiple detector computed tomography (MDCT) technique is of the form
BMD=m*[BMD(CT)]+b, where BMD(CT) refers to the determined thoracic trabecular BMD measurement and each of m and b are the different constants which are representative of different quantitative factors associated with normalization of BMD, and constant for a given CT scanner and tissue density.

9. The system of claim 8, wherein the constant m is different for different CT scanner models for a given tissue density, and m is determined for a specific CT scanner model.

10. A non-transitory machine readable medium containing a set of instructions that when executed cause a computing device to perform a method for determining bone mineral density (BMD) using quantitative computed tomography without a calibration phantom, the method comprising:
obtaining image data representing a heart from a scan performed by a computed tomography (CT) scanner;
using the image data, calculating a BMD at two or more spine levels by:
identifying a spine level at a position corresponding to a site of origin of an identified left main coronary artery in the image data; and
calculating a BMD based on computed tomography Hounsfield Unit (CTHU) values computed from a portion of the image data associated with the spine level at the position corresponding to the site of origin of the left main coronary artery and CTHU values computed from portions of the image data associated with one or more additional, consecutive, and different spine levels; and
determining a thoracic trabecular BMD measurement based on the BMD calculations at the spine level at the position corresponding to the site of origin of the left main coronary artery and the one or more additional, consecutive, and different spine levels, wherein the thoracic trabecular BMD measurement is normalized to a BMD determined by a multiple detector computed tomography (MDCT) technique using a translation formula based on at least one prior MDCT measurement such that the thoracic trabecular BMD measurement is determined without a calibration phantom, wherein the translation formula used to normalize the thoracic trabecular BMD measurement to the BMD determined by the multiple detector computed tomography (MDCT) technique includes two different constants, each of which are representative of a different quantitative factor associated with normalization of BMD, and constant for a given CT scanner and tissue density.

11. The method of claim 10, wherein the translation formula used to normalize the thoracic trabecular BMD measurement to the BMD determined by the multiple detector computed tomography (MDCT) technique is of the form
BMD=m*[BMD(CT)]+b, where BMD(CT) refers to the determined thoracic trabecular BMD measurement and each of m and b are the different constants which are representative of different quantitative factors associated with normalization of BMD, and constant for a given CT scanner and tissue density.

12. The method of claim 11, wherein the constant m is different for different CT scanner models for a given tissue density, and m is determined for a specific CT scanner model.

13. A method for determining bone mineral density (BMD) using phantomless quantitative computed tomography, the method comprising:
obtaining image data representing a heart and a thoracic spine from a scan performed by a computed tomography (CT) scanner, the scan being performed without a calibration phantom;
using the image data, calculating, with a computer, a BMD at three consecutive thoracic spine levels based on computed tomography Hounsfield Unit (CTHU) values computed from portions of the image data associated with each of the three consecutive thoracic spine levels including a first spine level, a second spine level, and a third spine level; and
determining, using the computer, a thoracic trabecular BMD measurement based on each of the BMD calculations at the first spine level, the second spine level, and the third spine level, wherein the thoracic trabecular BMD measurement is normalized to a BMD determined by a multiple detector computed tomography (MDCT) technique using a formula based on at least one previous calibration phantom measurement,
wherein the formula used to normalize the thoracic trabecular BMD measurement to the BMD determined by the multiple detector computed tomography (MDCT) technique includes two different constants, each of which are representative of a different quantitative factor associated with normalization of BMD, and constant for a given CT scanner and tissue density.

14. The method of claim 13, wherein the image data comprises a CT image showing the heart and the thoracic spine.

15. The method of claim 13, wherein the image data comprises CT image data representing a left main coronary artery and the three thoracic spine levels, wherein the first thoracic spine level is at a position corresponding to a site of origin of the left main coronary artery.

16. The method of claim 13, wherein the CT image data is obtained at a temporal resolution of less than 400 milliseconds/rotation.

17. The method of claim 13, wherein the formula used to normalize the thoracic trabecular BMD measurement to the BMD determined by the multiple detector computed tomography (MDCT) technique is of the form
BMD=m*[BMD(CT)]+b, where BMD(CT) refers to the determined thoracic trabecular BMD measurement and each of m and b are the different constants which are representative of different quantitative factors associated with normalization of BMD, and constant for a given CT scanner and tissue density.

18. A system configured for determining bone mineral density (BMD) using phantomless quantitative computed tomography, the system comprising:
one or more processors configured by computer readable instructions to:
obtain image data representing a heart and a thoracic spine from a scan performed by a computed tomography (CT) scanner, the scan being performed without a calibration phantom;
using the image data, calculate a BMD at three consecutive thoracic spine levels based on computed tomography Hounsfield Unit (CTHU) values computed from portions of the image data associated with the three consecutive thoracic spine levels including a first spine level, a second spine level, and a third spine level; and
determining a thoracic trabecular BMD measurement based on the BMD calculations at the first spine level, the second spine level, and the third spine level, wherein the thoracic trabecular BMD measurement is normalized to a BMD determined by a multiple detector computed tomography (MDCT) technique using a formula based on at least one previous calibration phantom measurement,
wherein the formula used to normalize the thoracic trabecular BMD measurement to the BMD determined by the multiple detector computed tomography (MDCT) technique includes two different constants, each of which are representative of a different quantitative factor associated with normalization of BMD, and constant for a given CT scanner and tissue density.

19. The method of claim 18, wherein the formula used to normalize the thoracic trabecular BMD measurement to the BMD determined by the multiple detector computed tomography (MDCT) is of the form
BMD=m*[BMD(CT)]+b, where BMD(CT) refers to the determined thoracic trabecular BMD measurement and each of m and b are the different constants which are representative of different quantitative factors associated with normalization of BMD, and constant for a given CT scanner and tissue density.

20. A non-transitory machine readable storage medium containing a set of instructions that when executed cause a computing device to perform a method for determining bone mineral density (BMD) using phantomless quantitative computed tomography, the method comprising:
obtaining image data representing a heart and a thoracic spine from a scan performed by a computed tomography (CT) scanner, the scan being performed without a calibration phantom;
using the image data, calculating a BMD at three consecutive thoracic spine levels based on computed tomography Hounsfield Unit (CTHU) values computed from portions of the image data associated with the three consecutive thoracic spine levels including a first spine level, a second spine level, and a third spine level; and
determining a thoracic trabecular BMD measurement based on the BMD calculations at the first spine level, the second spine level, and the third spine level, wherein the thoracic trabecular BMD measurement is normalized to a BMD determined by a multiple detector computed tomography (MDCT) technique using a formula based on at least one previous calibration phantom measurement,
wherein the formula used to normalize the thoracic trabecular BMD measurement to the BMD determined by the multiple detector computed tomography (MDCT) technique includes two different constants, each of which are representative of a different quantitative factor associated with normalization of BMD, and constant for a given CT scanner and tissue density.

21. The method of claim 20, wherein the formula used to normalize the thoracic trabecular BMD measurement to the BMD determined by the multiple detector computed tomography (MDCT) is of the form BMD=m*[BMD(CT)]+b, where BMD(CT) refers to the determined thoracic trabecular BMD measurement and each of m and b are the different constants which are representative of different quantitative factors associated with normalization of BMD, and constant for a given CT scanner and tissue density.

* * * * *